United States Patent
Dixon et al.

(10) Patent No.: US 11,612,379 B2
(45) Date of Patent: Mar. 28, 2023

(54) IMAGING SCAN HEAD APPARATUS HAVING A FLUID CHAMBER WITH AN INDUCTIVE POSITION SENSOR AND A GEARLESS VOICE-COIL MOTOR MECHANISM

(71) Applicant: Rivanna Medical LLC, Charlottesville, VA (US)

(72) Inventors: Adam Dixon, Charlottesville, VA (US); Frank William Mauldin, Charlottesville, VA (US); Kevin Owen, Crozet, VA (US)

(73) Assignee: Rivanna Medical, Inc., Charlottesville, VA (US)

( * ) Notice: Subject to any disclaimer, the term of this patent is extended or adjusted under 35 U.S.C. 154(b) by 65 days.

(21) Appl. No.: 17/032,382

(22) Filed: Sep. 25, 2020

(65) Prior Publication Data

US 2021/0085291 A1   Mar. 25, 2021

Related U.S. Application Data

(60) Provisional application No. 62/905,556, filed on Sep. 25, 2019.

(51) Int. Cl.
*A61B 8/00* (2006.01)
*A61B 8/08* (2006.01)

(52) U.S. Cl.
CPC .......... *A61B 8/4461* (2013.01); *A61B 8/5207* (2013.01); *A61B 8/483* (2013.01)

(58) Field of Classification Search
CPC ...... A61B 8/4461; A61B 8/5207; A61B 8/483
See application file for complete search history.

(56) References Cited

U.S. PATENT DOCUMENTS

| | | | | |
|---|---|---|---|---|
| 4,841,979 A | * | 6/1989 | Dow | A61B 8/445 600/446 |
| 5,844,140 A | * | 12/1998 | Seale | G01N 29/2456 73/620 |
| 7,225,678 B2 | * | 6/2007 | Kandler | G01L 19/0645 73/753 |
| 2005/0154311 A1 | * | 7/2005 | Bruestle | G10K 11/352 600/459 |
| 2007/0293761 A1 | * | 12/2007 | Wickline | A61B 8/12 600/459 |

(Continued)

FOREIGN PATENT DOCUMENTS

WO   WO-2010140126 A2 * 12/2010 ............. A61B 1/041

*Primary Examiner* — Joel Lamprecht
*Assistant Examiner* — Nyrobi Celestine
(74) *Attorney, Agent, or Firm* — Woods Rogers Vandeventer Black PLC; Nathan A. Evans (57) ABSTRACT

An ultrasound imaging scan head includes a fluid chamber including a gearless voice-coil motor therein. The voice-coil motor mechanism includes a rigid mechanical assembly, capable of moving with the fluid chamber, having one or more transducer elements and motor windings. Within the fluid chamber are motor magnets physically separated from the rigid mechanical assembly. The ultrasound imaging scan head further includes an inductive position sensor and internal bladder wherein the one or more transducer elements are capable of moving within the fluid chamber when a current is passed through the motor windings in a presence of a magnetic field generated by the one or more motor magnets.

13 Claims, 7 Drawing Sheets

(56) References Cited

U.S. PATENT DOCUMENTS

| | | | | |
|---|---|---|---|---|
| 2008/0097403 A1* | 4/2008 | Donaldson | ........ | A61M 25/0147 604/528 |
| 2010/0324423 A1* | 12/2010 | El-Aklouk | ........... | A61B 8/4488 600/444 |
| 2013/0207517 A1* | 8/2013 | Naka | ....................... | A61B 8/546 310/334 |
| 2014/0107491 A1* | 4/2014 | Fearnot | ................. | G01S 15/894 600/463 |
| 2017/0153207 A1* | 6/2017 | Burchardt | ........... | G01S 15/8931 |
| 2018/0317883 A1* | 11/2018 | Huhtamaki | .......... | A61B 8/4455 |

\* cited by examiner

IMAGING SCAN HEAD APPARATUS HAVING A FLUID CHAMBER WITH AN INDUCTIVE POSITION SENSOR AND A GEARLESS VOICE-COIL MOTOR MECHANISM

CROSS-REFERENCE TO RELATED APPLICATION

The present application relies on the disclosures of and claims priority to and the benefit of the filing dates of U.S. Provisional Application No. 62/905,556, filed Sep. 25, 2019. The disclosures of that application are hereby incorporated by reference herein in their entireties.

STATEMENT REGARDING FEDERALLY SPONSORED RESEARCH

This invention was made with government support under Grant No. R44GM123791 awarded by the National Institutes of Health (NIH) National Institute of General Medical Sciences (NIGMS). The government has certain rights in the invention.

TECHNICAL FIELD

The present invention is related to a scan head apparatus that may be used to mechanically translate or orient a transducer element or array in one or more degrees of freedom.

BACKGROUND

In medical ultrasound imaging, the ultrasound transducer is often mounted within a scan head apparatus. The scan head apparatus contains a mechanical motor mechanism that changes the position of the transducer within the scan head so that ultrasound images may be acquired from different positions. The benefit of this technique is to increase the field of view of the ultrasound image, such as by extending a 1D image line to a 2D image field of view or a 2D imaging field of view to a 3D imaging field of view. In one common example, the motorized scan head is used to scan a single element transducer along a linear path so that image lines at each position of the path may be acquired in order to form a 2D ultrasound image. In another common example, the motorized scan head may be used to translate a 1D transducer array in order to collect three-dimensional ultrasound data.

Existing scan heads are constructed with geared direct current (DC) motor mechanisms and optical position encoders. Because ultrasound requires liquid coupling to transmit energy into the patient's body, the transducer element or array must be contained within a liquid chamber. However, optical position encoders cannot tolerate refraction effects of liquid and must operate in air. Therefore, the optical position encoder is oriented outside the liquid chamber with the DC motor shaft inside the chamber and a liquid seal in between. Scan head liquid chambers must not leak, or else air can enter the chamber, thus preventing adequate ultrasound transmission. Additionally, scan heads must tolerate operating and storage temperature ranges of up to 60° C. Due to fluid expansion effects, in order to prevent scan head leaks, a bladder mechanism, often external to the fluid chamber, is required. Due to the aforementioned design requirements, existing scan heads are large, heavy, prone to leaks, and expensive.

SUMMARY

The present invention overcomes limitations referenced above with a scan head mechanism that is ultra-compact, light, less prone to leaks, and low cost. The scan head invention is based on a gearless voice-coil motor mechanism, inductive position detection, and internal bladder. Because no contact is needed between transducer element, motor mechanism, and position sensor, the design is very compact, and therefore, light weight. The entire mechanism is contained within a small fluid chamber including the bladder. Because there is no gasket or seal mechanism between major components, the invention is also less susceptible to leaks.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention. For a fuller understanding of the nature and advantages of the present technology, reference is made to the following detailed description of preferred embodiments and in connection with the accompanying drawings, in which.

DETAILED DESCRIPTION

Scan heads are used in a variety of applications. For example, in medical or clinical applications, scan heads may be used for medical imaging functions. In this non-limiting example, an imaging transducer is disposed within a scan head so as to deliver a pulse, tone, sequence or programmed energy signal into a target location to be imaged. A specific example is one or more ultrasound transducer elements that deliver an ultrasound signal into a patient's body and detect a return signal therefrom so as to form a computer-generated image of the target region. Different ultrasound imaging modes can be utilized, depending on a given application and design as known to those skilled in the art. The present disclosure can be used in medical ultrasound applications but is not limited to this application. Those skilled in the art will appreciate that a variety of types of transducers, signal transmitters and/or receivers and other arrays can also benefit from the present invention, which are comprehended hereby.

Figure 1:
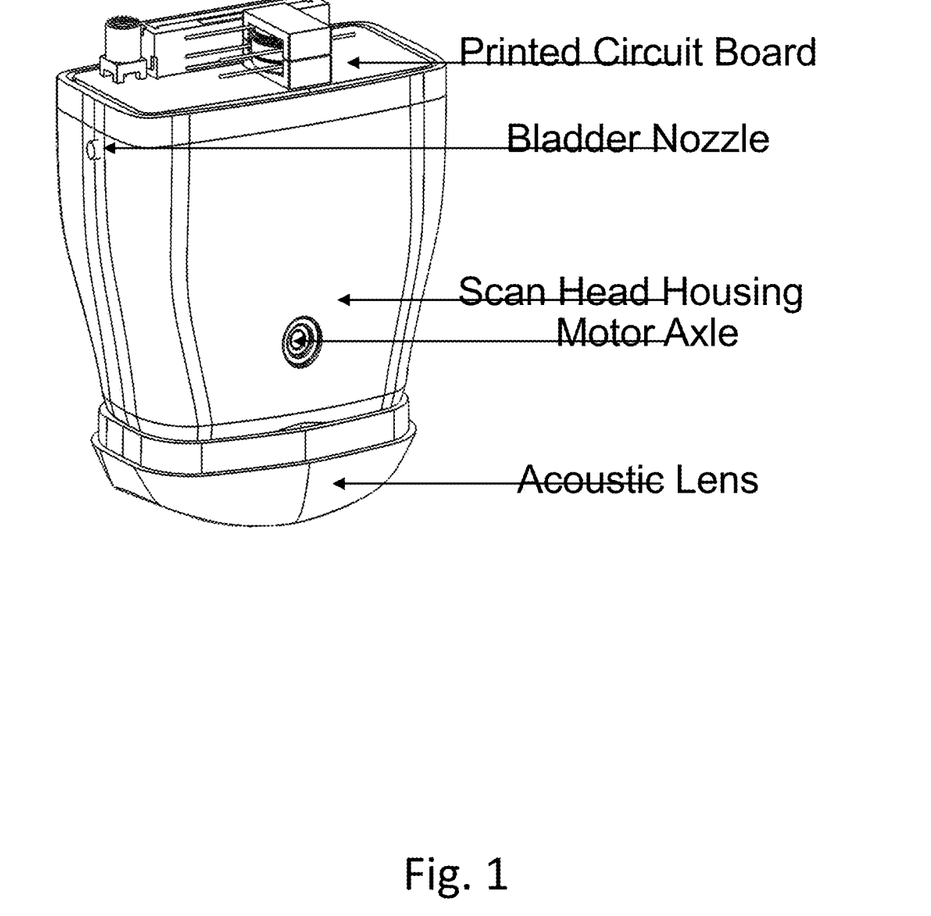
FIG. 1 depicts the exterior of the scan head assembly.

In one exemplary embodiment, the exterior of a scan head assembly is depicted in FIG. 1. Ultrasonic energy is transmitted from an ultrasound transducer(s) located within the Scan Head Housing, through the Acoustic Lens, and into the patient. The Acoustic Lens has material properties that promote low absorption, low reflection, and low attenuation of the acoustic energy. The Scan Head Housing provides both a scaffold for positioning internal components (e.g. Motor Axle), and a physical barrier for containing the acoustic transmission fluid within the scan head assembly. The internal bladder contains a Bladder Nozzle that protrudes from the outer wall of the Scan Head Housing and provides a means by which the inside of the bladder is maintained at approximately atmospheric pressure. The Printed Circuit Board, located at the top of the assembly, provides both a lid to contain the fluid within the scan head assembly and also electronics to control motor functions, inductively coupled angular sensor functions, and acoustic imaging functions.

It should be understood that the exemplary embodiments provided and illustrated herein are merely given for the sake of full understanding of the various aspects of the invention. Variations and many similar or equivalent embodiments can be devised based on this disclosure, any and all of which are encompassed hereby. For example, the shape, form factor and other mechanical and/or electronic configurations are equally possible. As an example, the placement of circuit boards used in the present examples with respect to the other components is for illustrative purposes, to achieve certain advantages in some non-exhaustive embodiments, and are not to be understood as a limiting or required aspect of all embodiments hereof.

Figure 2:
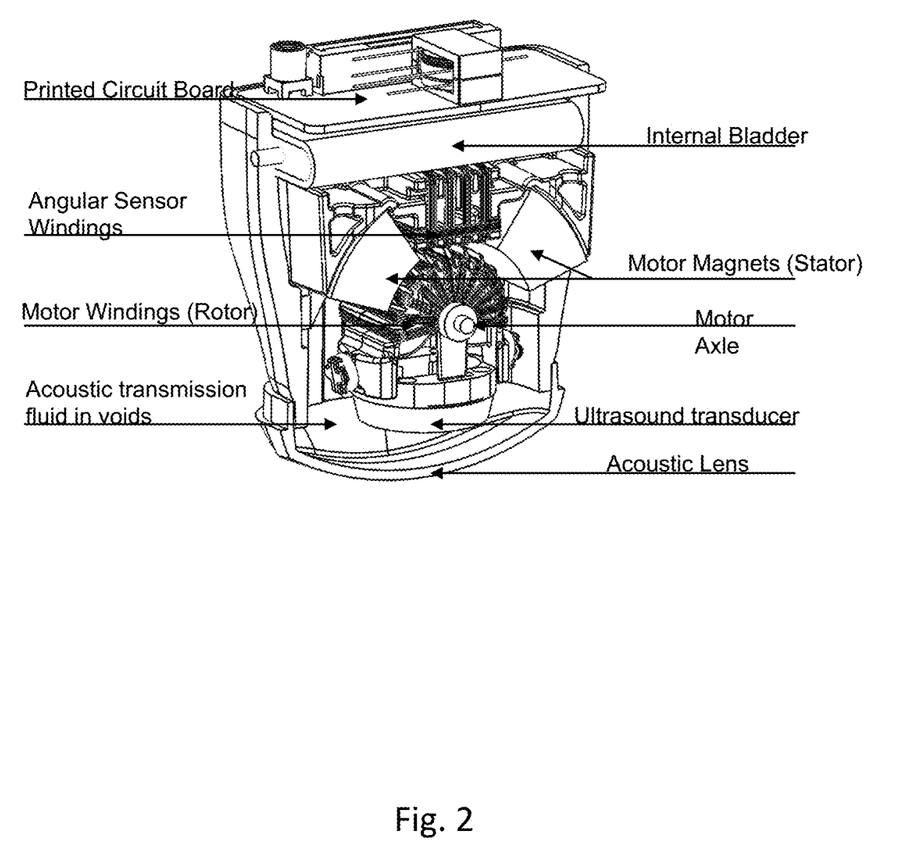
FIG. 2 depicts a cutaway to show internal components of the scan head assembly.

The internal components of the Scan Head Assembly depicted in FIG. 2 provide the following functionalities: ultrasound transmission/reception, motor mechanisms for sweeping the ultrasound transducer(s) along a predefined path, inductively coupled position sensor. In one or more examples the position is an angular position, and the position sensor is an angular position sensor. In one or more examples a pressure compensator is used for pressure compensation to account for thermal expansion/contraction of the acoustic transmission fluid.

Figures 3A, 3B, 3C:
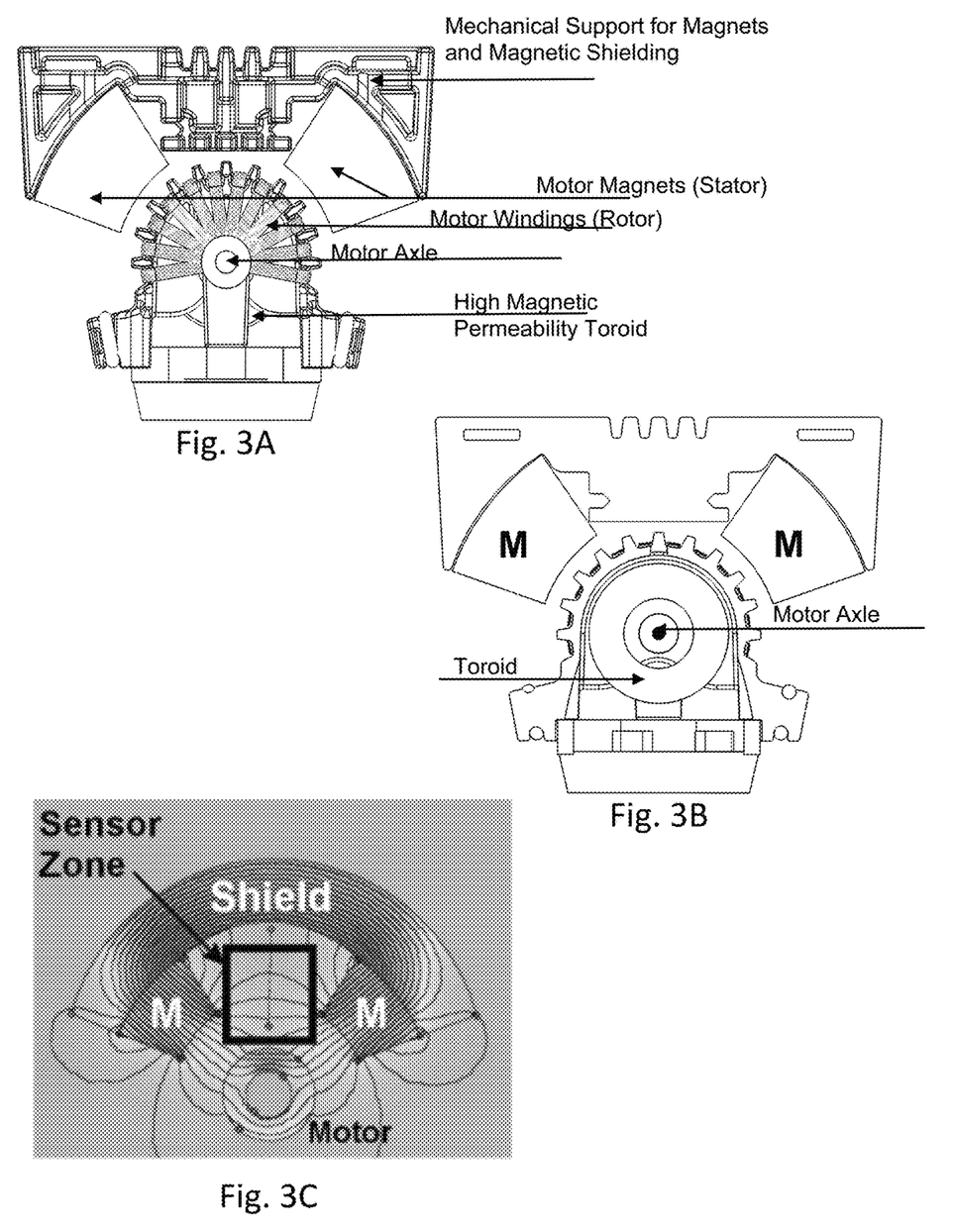
FIGS. 3A, 3B, and 3C depict motor function of the invention.

As seen in FIGS. 3A-C, a voice coil motor function is achieved by passing DC current through the Motor Windings, in the presence of a constant magnetic field provided by the permanent Motor Magnets. Motor direction may be changed by reversing the direction of electrical current through the motor windings. Motor efficiency is improved by placing a High Magnetic Permeability Toroid within the center of the motor windings to focus the magnetic field lines on the current carrying Motor Windings. A magnetic shield, comprised of a soft magnetic material (e.g., SS416), may also be incorporated to both focus magnetic field lines in the area of motor function and to also shield the motor and angular sensor functions from the presence of external sources of magnetic interference.

Figure 4:
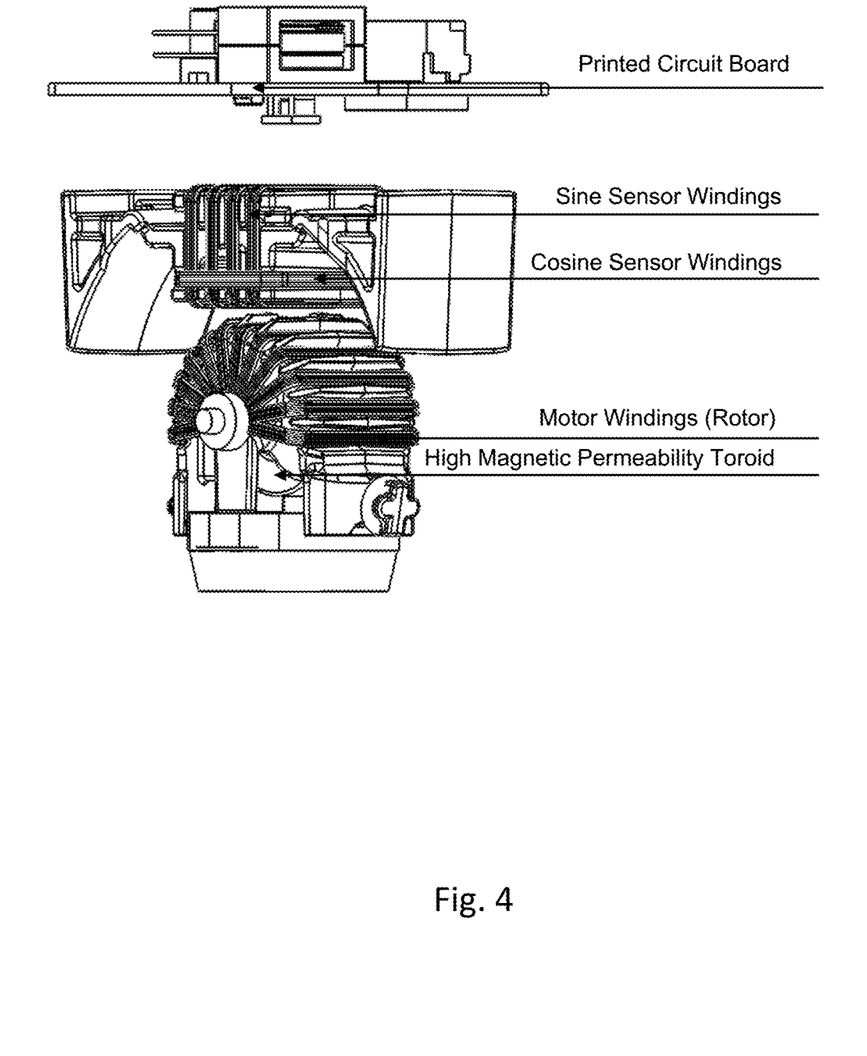
FIG. 4 depicts an inductively coupled angular sensor function.

The angular position of the motor rotor is sensed via the inductive coupling between the Motor Windings and the Sine and Cosine Sensor Windings, as shown in FIG. 4. A radio frequency excitation current is passed through the motor windings, and some of this electromagnetic energy is inductively coupled into the Sine and Cosine Sensor Windings. The inductively coupled energy produces a voltage in the Sine and Cosine Sensor Windings, which varies with the angular position of the motor rotor. The electronic componentry required to produce the radio frequency excitation signal and to measure and analyze the voltage signals measured by the Sine and Cosine Sensor Windings is housed on the Printed Circuit Board. The presence of a High Magnetic Permeability Toroid located in the center of the Motor Windings increases the inductance of the motor windings and increases the efficiency of inductively coupled energy transfer between the motor windings and the sensor windings. This serves to increase the signal to noise ratio of the inductive angular position sensor. Other sensor types can be employed as suits a particular embodiment or application.

The angular position of the motor rotor may be measured in real time by the inductive sensor or sensors, and the motor drive current is modulated as required in order to maintain the desired motor angular velocity.

The angular sensor assembly may undergo a calibration process in which the angular position reported by the inductive sensor is matched to a known angular position defined by an independent calibration system. This calibration process is intended to account for minor variations in motor windings, sensor windings, and the relative physical positions of individual components within the scan head assembly.

While the present examples are illustrated by way of angular positioning, angular sensing and motors providing rotational (angular) displacement, some or all features hereof can be adapted for linear or other motion and sensing as would be appreciated by those skilled in the art upon review of the present description and examples. Therefore, the present invention should not be limited to angular movement and sensing unless it is expressly stated or otherwise logically required by the given context.

Figure 5:
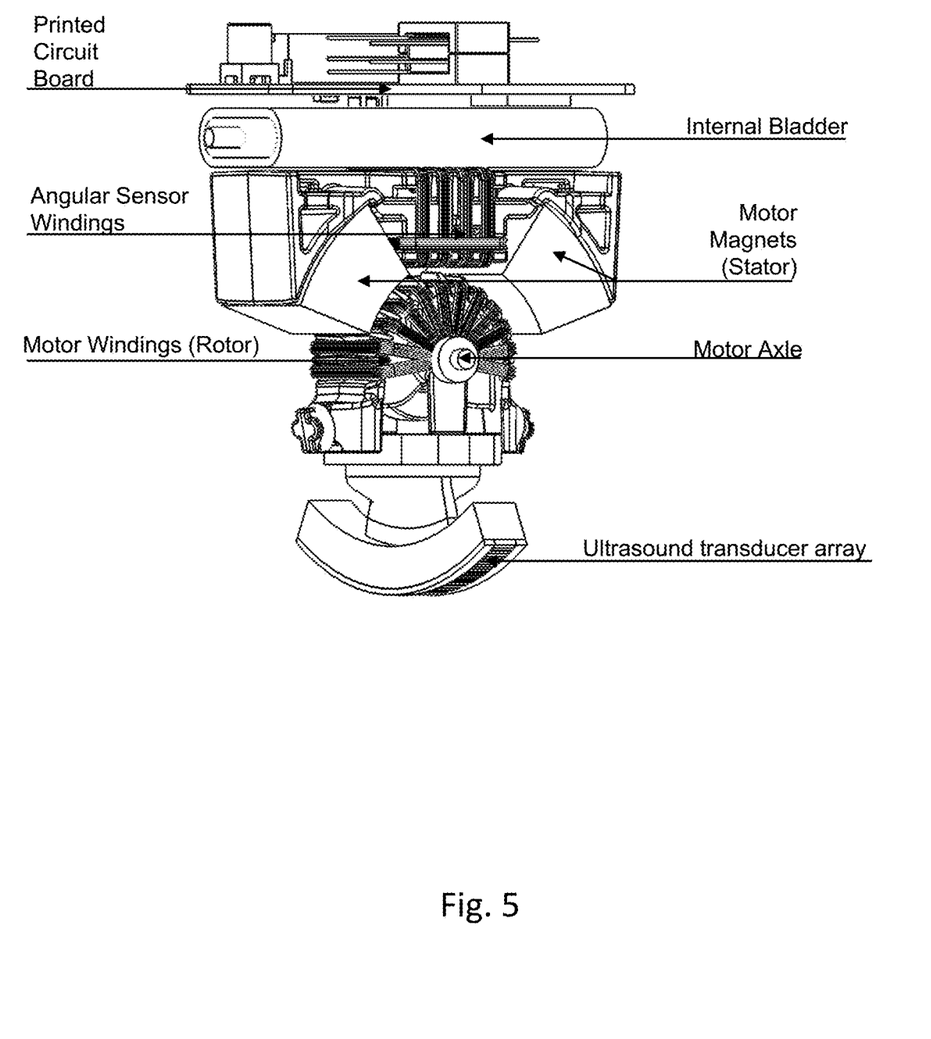
FIG. 5 is a three-dimensional imaging scan head with exemplary incorporation of ultrasound transducer array.

In some embodiments, the Scan Head Assembly may include a transducer such as an ultrasound transducer array that contains more than one individual ultrasound transducer element, as can be seen in FIG. 5. A construction shown in FIG. 5. is capable of imaging a three-dimensional volume when the array is swept angularly by the voice coil motor.

Figure 6:
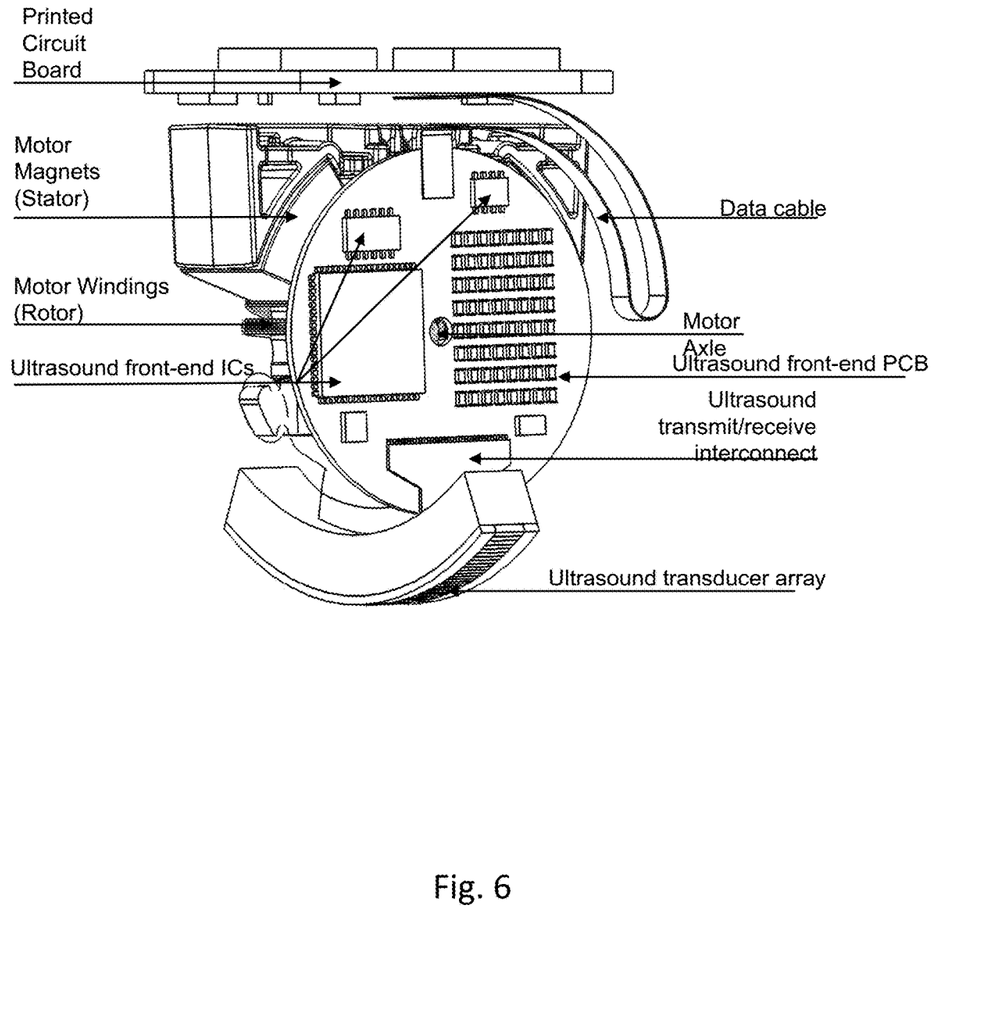
FIG. 6 depicts incorporation of ultrasound front-end electronics within scan head internal components.

The Scan Head Assembly may optionally include additional electronics located within the internal componentry that manages the transmission and reception of ultrasonic signals from one or more ultrasound transducers associated with the internal componentry. As shown in FIG. 6, the electronics may optionally be incorporated on a PCB located within the scan head assembly. The PCB may be affixed to the motor stator (and therefore be stationary) or may be affixed to the motor rotor (and therefore rotate with the motor and ultrasound transducer array). Electrical connections to the ultrasound array, ultrasound front-end PCB(s), and additional printed circuit board may be provided by high flex-life electrical interconnect cables.

Figure 7:
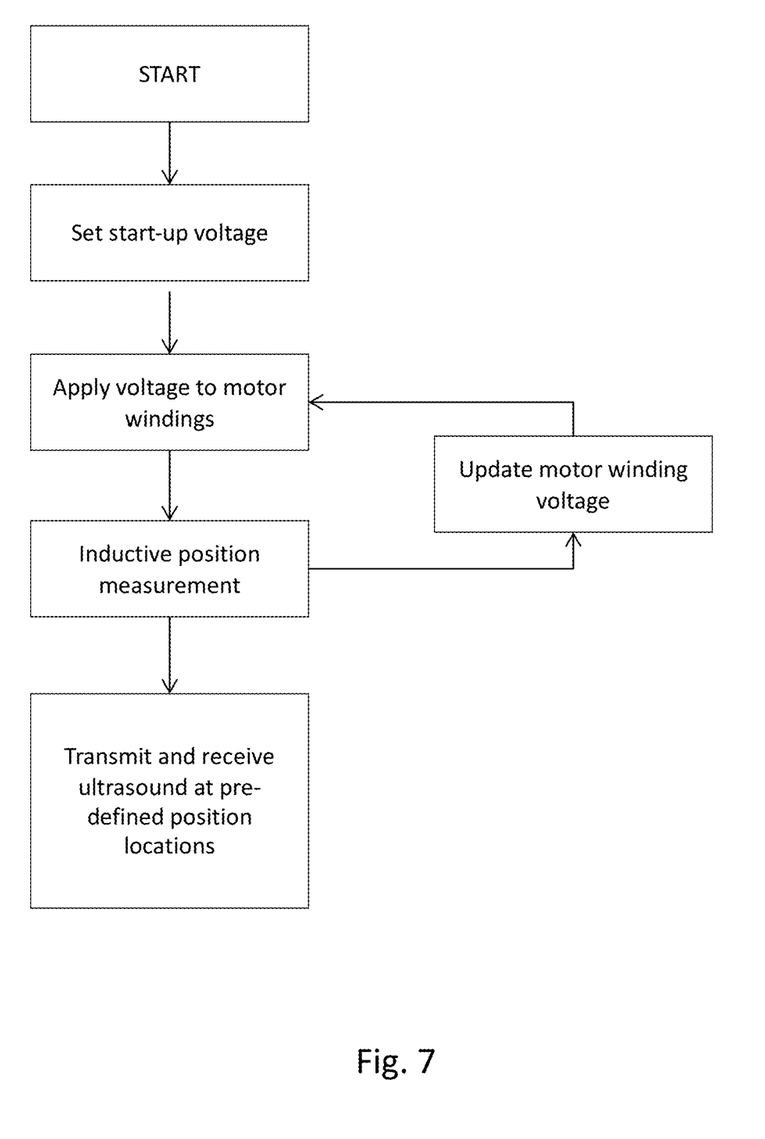
FIG. 7 shows a block diagram of an exemplary embodiment of the assembly.

In FIG. 7, a motor voltage control system is executed on a processor unit connected to, or embedded within, the scan head apparatus. In aspects, the ultrasound transmit and receive circuitry is typically a separate processor unit connected to, or embedded within, the scan head apparatus. In aspects, the connected processor may be connected wirelessly or by wire.

Embodiments of the invention may be configured and arranged to or may comprise one or more of the following features: using an inductively coupled angular position sensor; measuring a radio frequency signal of its own origin to determine the angular position of the motor rotor; the radio frequency signal employed for angular position sensing is transmitted in the motor rotor windings, thereby constituting direct integration of the angular position sensor with the motor drive electronics; incorporation of a compressible, internal air-filled bladder to compensate for thermal expansion/compression of the acoustic transmission fluid; incorporation of high magnetic permeability componentry to improve motor function and increase angular sensor signal to noise ratio; incorporation of soft magnetic materials to provide immunity to external sources of magnetic interference and to improve the efficiency of the motor magnetic circuit; incorporation of one or more ultrasound transducer elements to provide 2D or 3D imaging; and integration of ultrasound front-end electronics directly within the fluid-filled chamber of the scan head to increase compactness of the design and to reduce complexity of electrical interconnects.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. An imaging scan head apparatus comprising:
a fluid chamber, wherein the fluid chamber comprises:
a gearless voice-coil motor mechanism comprising:
a rigid mechanical assembly capable of moving within a fluid within the fluid chamber comprising:
one or more transducer elements; and motor windings; and
one or more motor magnets physically separated from the rigid mechanical assembly;
an inductive position sensor; and
an internal bladder contained within the fluid chamber and engaging with the fluid of the fluid chamber; and
a printed circuit board external to the fluid chamber, wherein a first side of the printed circuit board engages the fluid of the fluid chamber and a second side of the printed circuit board is separated from engagement with the fluid in the fluid chamber;
wherein the internal bladder is located between the printed circuit board and the components in the fluid chamber;
wherein the one or more transducer elements are capable of moving within the fluid chamber when a current is passed through the motor windings in a presence of a magnetic field generated by the one or more motor magnets; and
wherein the one or more transducer elements, the one or more motor magnets, and the inductive position sensor are separated by a physical distance from one another.

2. The imaging scan head apparatus according to claim 1, wherein the one or more transducer elements are configured to provide two-dimensional (2D) or three-dimensional (3D) imaging.

3. The imaging scan head apparatus according to claim 1, further comprising ultrasound front-end electronics within the fluid chamber in a manner that provides for a decrease in size of the scan head imaging apparatus as compared with a scan head imaging apparatus with ultrasound front-end electronics outside of the fluid chamber.

4. The imaging scan head apparatus according to claim 1, further comprising ultrasound front-end electronics within the fluid chamber providing for a reduction in a complexity of, an amount of, or a number of electrical interconnects within or related to the scan head imaging apparatus.

5. The imaging scan head apparatus according to claim 1, wherein the inductive position sensor is capable of measuring a radio frequency signal transmitted by the inductive position sensor to determine an angular position of the motor windings.

6. The imaging scan head apparatus according to claim 5, wherein the radio frequency signal is capable of being transmitted directly to the motor windings.

7. The imaging scan head apparatus according to claim 1, wherein the inductive position sensor is configured to integrate or communicate with, by way of a radio frequency signal transmitted by the inductive position sensor, one or more electronics or receivers of the gearless voice-coil motor mechanism.

8. The imaging scan head apparatus according to claim 1, wherein the internal bladder is a compressible gas-filled bladder.

9. The imaging scan head apparatus according to claim 1, wherein the internal bladder is configured to compensate for or regulate thermal expansion or compression of acoustic transmission fluid contained within the fluid chamber.

10. The imaging scan head apparatus according to claim 1, further comprising componentry with magnetic permeabilities capable of improving functionality or increasing performance capabilities of the gearless voice-coil motor mechanism as compared with a gearless voice-coil motor mechanism without componentry with magnetic permeabilities.

11. The imaging scan head apparatus according to claim 1, further comprising magnetic permeability componentry capable of increasing signal-to-noise ratio measured by the inductive position sensor.

12. The imaging scan head apparatus according to claim 1, further comprising soft magnetic materials capable of providing partial or complete immunity from or mitigation of external sources of magnetic interference.

13. The imaging scan head apparatus according to claim 1, further comprising soft magnetic materials capable of improving or increasing efficiency or performance of the gearless voice-coil motor mechanism or a motor magnetic circuit as compared with a gearless voice-coil motor mechanism or a motor magnetic circuit without soft magnetic materials.

* * * * *